(12) United States Patent
Hunicke-Smith et al.

(10) Patent No.: US 6,374,683 B1
(45) Date of Patent: Apr. 23, 2002

(54) PIPETTER

(75) Inventors: Scott P. Hunicke-Smith, Menlo Park; Omar Medeiros, Mountain View, both of CA (US)

(73) Assignee: Genomic Instrumentation Services, Inc., San Carlos, CA (US)

( * ) Notice: Subject to any disclaimer, the term of this patent is extended or adjusted under 35 U.S.C. 154(b) by 0 days.

(21) Appl. No.: 09/493,429

(22) Filed: Jan. 29, 2000

Related U.S. Application Data

(60) Provisional application No. 60/118,013, filed on Jan. 29, 1999.

(51) Int. Cl.[7] .................................................. B01L 3/02
(52) U.S. Cl. .................................. 73/864.17; 73/863.32
(58) Field of Search .......................... 73/864.17, 863.32

(56) References Cited

U.S. PATENT DOCUMENTS

| | | |
|---|---|---|
| 3,650,306 A | 3/1972 | Lancaster |
| 4,106,911 A | 8/1978 | Marcelli |
| 4,444,062 A | 4/1984 | Bennett et al. |
| 4,554,839 A | 11/1985 | Hewett et al. |
| 4,671,123 A | 6/1987 | Magnussen et al. |
| 4,833,384 A | 5/1989 | Munro et al. |
| 5,021,217 A | 6/1991 | Oshikubo |
| 5,193,403 A | 3/1993 | Burgisser |
| 5,343,909 A | 9/1994 | Goodman |
| 5,406,856 A | 4/1995 | Kuhn et al. |
| 5,413,006 A | 5/1995 | D'Autry et al. |
| 5,456,879 A | 10/1995 | Suovaniemi |
| 5,470,538 A | 11/1995 | Lind |
| 5,505,097 A | 4/1996 | Suovaniemi et al. |
| 5,540,889 A | 7/1996 | Gordon et al. |
| 5,763,278 A | 6/1998 | Sickinger et al. |
| 6,146,594 A | 11/2000 | De Graaff et al. ......... 422/100 |

Primary Examiner—Thomas P. Noland
(74) Attorney, Agent, or Firm—Seed Intellectual Property Law Group PLLC

(57) ABSTRACT

A micropipetter a plurality of hollow needles to deliver fluid, the needles being anchored in a sample block; a needle guide assembly with a plurality of needle guide shafts and compression springs attached at one end to the sample block and at the other end to a needle guide plate, each spring surrounding a needle guide shaft, and the needle guide plate controlling the spacing of the needles; a sample block having a plurality of hollow, tapered spaces, each of which connect with the hollow needle; a displacement volume block having a plurality of hollow spaces, each being occupied by a piston pin, each piston pin being sealed with a stationary seal assembly; a stationary sheet seal located between the sample block and the displacement volume block, the sheet seal having a plurality of holes corresponding to and separating the spaces in the sample block and the displacement volume block, such that precise volume displacement is provided; a seal constraint plate located above the displacement volume block, the seal constraint plate positioned to hold in place an airtight, low-friction seal assembly around each of the piston pins; the piston pins being attached to a piston pin plate; and a motive means for moving the pistons vertically and thereby alternately aspirating fluid into the needles and dispensing fluid from the needles. The seal assembly has at least one sleeve and one O-ring. The motive means is at least one motor having at least one lead-screw drive which goes through the core of the motor, the lead-screw drive being attached to an armature, such that actuating the motor causes the lead-screw drive to pull up or lower the rest of the micropipetter. Optionally, the micropipetter has at least one set of crossbars, each crossbar being attached to the constraint plate and the piston pin plate to increase stability and precise movement. The micropipetter needles can number 1, 8, 16, 24, 96, 384 or 1536. Optionally, the micropipetter has a counter-balance to aid in hand-held use.

11 Claims, 5 Drawing Sheets

PIPETTER

This application claims the benefit of U.S. Provisional Application No. 60/118,013, filed Jan. 29, 1999.

TECHNICAL FIELD

This invention relates to an improved device for automated pipetting of small volumes of liquid.

BACKGROUND OF THE INVENTION

Today there is a great demand for high-throughput biological and chemical synthesis, analysis and sample processing. In chemical and biological laboratories, sample transfer from a source plate to a target plate (or piece of lab ware) is a fundamental task. Typically a pipette or pipetter system is used to (i) collect a desired sample from the source piece of lab ware which holds the sample in one array format, and (ii) deliver/dispense the collected sample to the target piece of lab ware in the same or another array format. During the transfer of samples, it is extremely important to dispense and aspirate precise volume samples and to avoid their cross-contamination.

One pipetting device which addresses the need for high-throughput Hydra® Microdispenser (Robbins Scientific, Inc., Sunnyvale, Calif.) uses several syringes positioned together in a holder. The syringes utilized are made of high quality borosilicate glass, the inner chambers of the barrels are precision-machined and highly polished to ensure leak-free performance. The Teflon® tips used on the stainless steel plungers are ribbed to prevent liquid from leaking around the tip under pressure. Each needle of the pipetting apparatus is permanently fixed into a Teflon seal at the end of the syringe barrel. An array of these syringes requires large actuation forces because of the friction in the seals. The cost of each such syringe is also high due to the precise machining of the glass. Moreover, the use of movable seals on a syringe can lead to inconsistency in pressure on the samples result in imprecise volumes of sample.

Another pipetter system for pipetting in parallel is disclosed in U.S. Pat. No. 5,541,889. This system has an actuator which operates an upper plate assembly which holds a plurality of metal rods, such that all the rods are moved together along parallel longitudinal axes in respective tubes. It utilizes less actuation force than the previously disclosed invention by having the plurality of metal rods come in direct contact with the sample fluids for aspirating and dispersing. The actuator raises the upper plate assembly and the plurality of rods simultaneously traverse the length of their respective tubes for aspiration. For dispersion of the samples, the actuator is lowered very rapidly and stopped abruptly and in turn, the upper plate assembly is lowered very rapidly and stopped abruptly. This imparts a high velocity to the collected sample fluid within the tubes and the samples use their own inertia to exit the distal end of the tubes. The liquid samples involved in biological and chemical synthesis, analysis and sample processing are often corrosive could lead to the destruction of the metal rod design disclosed.

What is needed is an improved pipetting apparatus that is durable and capable of efficiently dispensing and aspirating multiple precise volumes of samples without the cross-contamination of samples.

SUMMARY OF THE INVENTION

The present invention addresses the problems of efficiency, purity, and precision of samples.

In a first embodiment, a micropipetter includes a plurality of hollow needles to deliver fluid, said needles being anchored in a sample block; a needle guide assembly comprising a plurality of needle guide shafts and compression springs attached at one end to the sample block and at the other end to a needle guide plate, each spring surrounding a needle guide shaft, and the needle guide plate guiding the spacing of the needles; a sample block having a plurality of hollow spaces, each of which connect with the hollow needle; a displacement volume block having a plurality of hollow spaces, each being occupied by a piston pin, each piston pin being sealed with a stationary seal assembly; a stationary sheet seal located between the sample block and the displacement volume block, the sheet seal having a plurality of holes corresponding to and separating the spaces in the sample block and the displacement volume block, such that precise volume displacement is provided; a seal constraint plate located above the displacement volume block, the seal constraint plate being positioned to hold in place an airtight, low-friction seal assembly around each of the piston pins; the piston pins being attached to a piston pin plate; and motive means for moving the pistons vertically and thereby alternately aspirating fluid into the needles and dispensing fluid from the needles.

In a further embodiment, the seal assembly has at least one sleeve which is in contact with the piston pin, at least one O-ring. The sleeve can be Teflon. The motive means is at least one motor having at least one lead-screw drive which goes through the core of the motor, the lead-screw drive being attached to an armature, such that actuating the motor causes the lead-screw drive to pull up or lower the rest of the micropipetter. The micropipetter further has at least one set of crossbars, each crossbar being attached to the constraint plate and the piston pin plate, thereby increasing stability of the micropipetter and aiding in precise movement. The hollow needles can number 1, 8, 16, 24, 96, 384 or 1536. The motive means can be controlled by an on-board microprocessor.

In yet another embodiment, the micropipetter can be provided with a counter-balance to aid in hand-held use.

In yet another embodiment, the disclosed micropipetter is incorporated into a robotic workstation.

DETAILED DESCRIPTION OF THE INVENTION

As used herein the terms "parallel pipetter" and "parallel pipetting", and the like mean simultaneous operation of a plurality of pipettes or similar devices. Said another way, these terms mean the collective operation of a plurality of pipettes (ie., operation at the same time as opposed to a serial or one-at-a-time operation).

One of the best ways to address the need for highly parallel sample processing in the field of biotechnology is a multi-channel pipetting device. While many multi-channel pipettes exist in the field, there are few that are capable of efficiently dispensing and aspirating multiple pure and precise volumes of samples.

One multi-channel pipette is made by Robbins Scientific (see Robbins Scientific web site, Hydra Microdispensers). This pipetting apparatus is made up of many barrels of glass syringes held in a fixed array along an X-Y grid that corresponds to the exact center of each well in a microplate. The plungers within the syringes move up and down under computer control, dispensing or aspirating liquid to or from microplates. Each Syringe has a plunger with a Teflon® seal at the attached to its distal end and another Teflon® seal at the distal end of the glass syringe. While these seals create an airtight chamber for air volume displacement and protect the plungers from contact with samples, the moving seal requires a great deal of force to overcome its friction. Moreover, the various points of friction are likely to wear at different rates, which can lead to imprecise volumes of sample aspirating and dispensing. In contrast, the present invention utilizes a stationary airtight seal. Therefore, there is less friction to overcome, and less power is needed to actuate the inventive pipetting apparatus. Moreover, a movable seal with great amounts of force acting upon it can potentially become shifted and allow sample contact with sensitive portions of the pipetting apparatus, such as the plungers.

Another system disclosed in U.S. Pat. No. 5,540,889 utilizes less power than the Robbins Scientific apparatus by not using seals and having its rods contact the liquid samples directly. While, this may be an efficient method for dispensing and aspirating samples, it can to parts corrosion of the pipetter due to repeated direct contact with samples. Moreover, it is likely that bits of the samples will remain on the rod after dispensing samples and lead to crosscontamination of samples.

Figure 1:
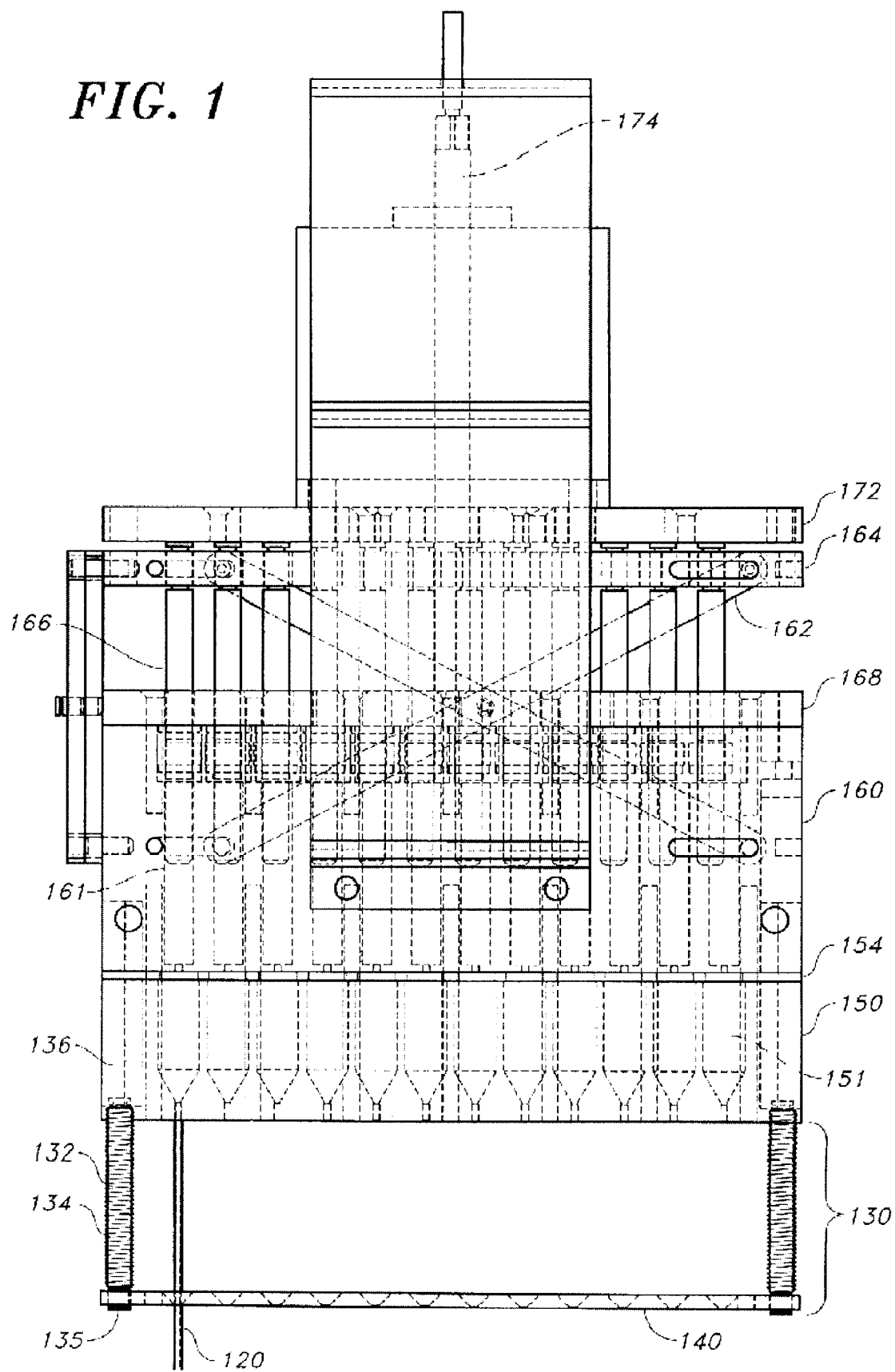
FIG. 1 is an overview of the pipetter.

FIG. 1 shows an overview of an embodiment of the micropipetter that can aspirate and dispenses precise volumes of fluid through 96 needles 120. There are lateral needle guide assemblies 130 on each corner of the sample block 150 to help guide the needles 120. The needle guide assemblies 130 are composed of a compression spring 132 around a solid needle guide shaft 134. For precise positioning, the needles 120 are also held in place by a needle guide plate 140, which the needle guide assembly 130 supports. The needle guide plate 140 has a plurality of holes to accommodate the plurality of needles 120 of the pipetting apparatus and the needle guide assemblies 130. The needle guide plate is preferably made of a non-corrosive metal. The needle guide plate 140 is held in place by rings 135 which attach to the ends of the needle guide assemblies 130 in each corner of the needle guide plate 140. As the needles 120 are lowered, the needle guide assemblies 130 recess up into hollow shafts 136 of the volume block 150 and the displacement volume block 160.

The sample volume block 150 is preferably made of Delrin AF® (Interstate Plastics) and is machined with 96 cylinders 151 to accommodate 96-well plate use. The cylinders 151 retain the liquid samples prior to dispensing and after aspirating samples. Above the sample volume block 150 is the displacement volume block 160 with hollow channels 161 to accommodate 96 pistons 166. Each hollow channel 161 of the displacement volume block lines up with a respective cylinder 151 of the sample volume block. Between the sample volume block 150 and the displacement volume block 160 is a sheet seal 154, which will be further discussed below. On top of the displacement volume block 160 is seal constraint plate 168 with a plurality of holes to allow the pistons 166 to slides through it. The seal constraint plate 168 will be discussed further below.

The piston pins 166 are mounted on piston pin plate 164. Connected to the piston pin plate 164 from above is upper piston plate 172. A crossbar linkage 162 attaches to the constraint plate 168 and the piston pin plate 164 by pins and there is one for each of the four sides of the pipetting apparatus, which helps stabilize the blocks and cause precise movement.

Figure 2:
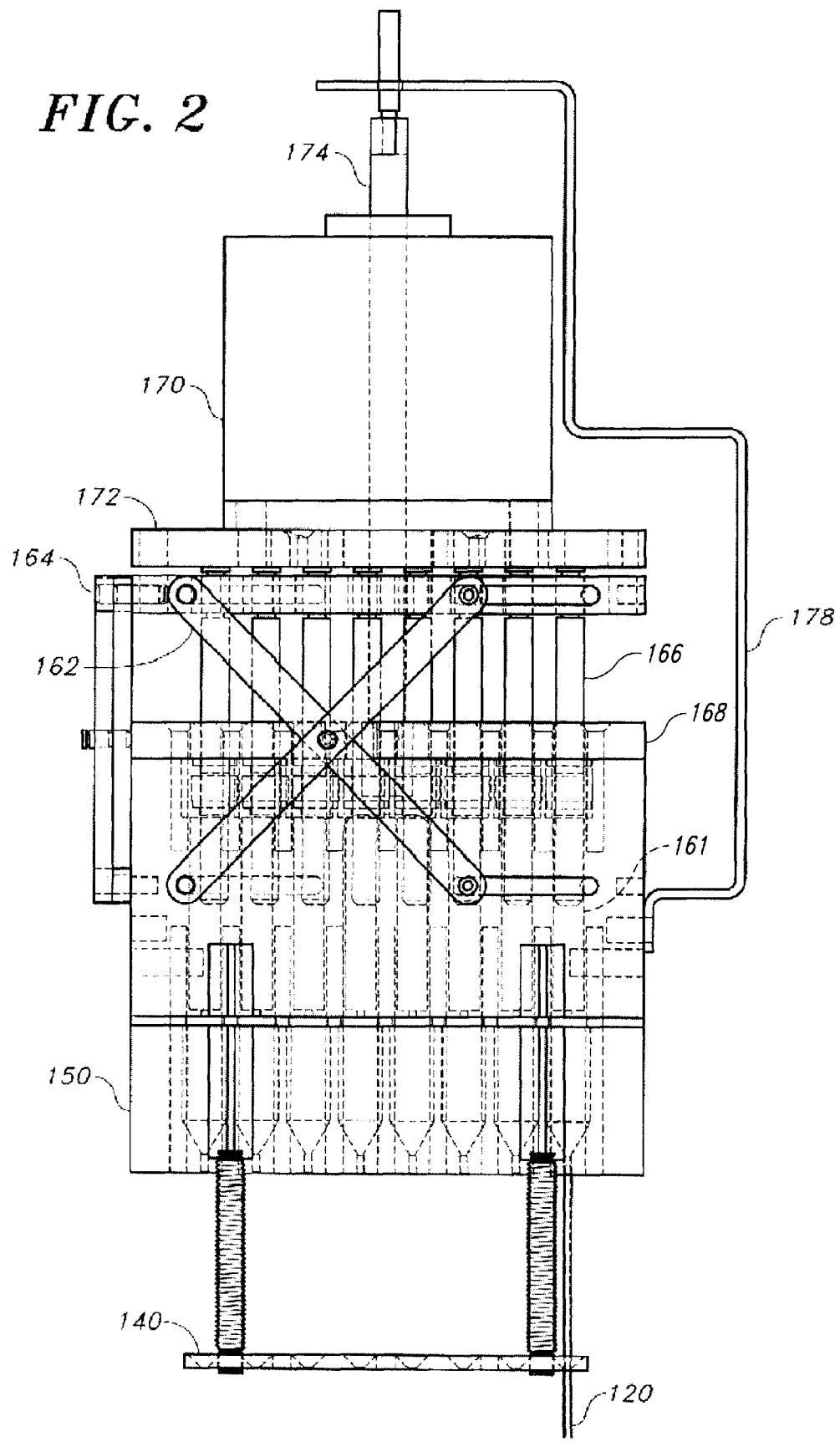
FIG. 2 is another view of the pipetter, rotated 90 degrees from FIG. 1.

In FIG. 2, the micropipetter is rotated 90 degrees from the view in FIG. 1. It illustrates the drive motor 170 which actuates vertical movement as it turns lead screw 174 that is held in place by a lead screw constraint bracket 178. The drive motor is controlled by a remote computer (not shown). As the lead screw 174 is turned, it pushes down or pulls up on the constraint plate 168, which is connected to the piston plate 164 and in turn pushes down or pulls up the piston pins 166. The piston pins 166 simultaneously vertically traverse the their respective hollow channels 161 of the displacement volume block 160 for aspiration and deposit of samples.

Figure 3:
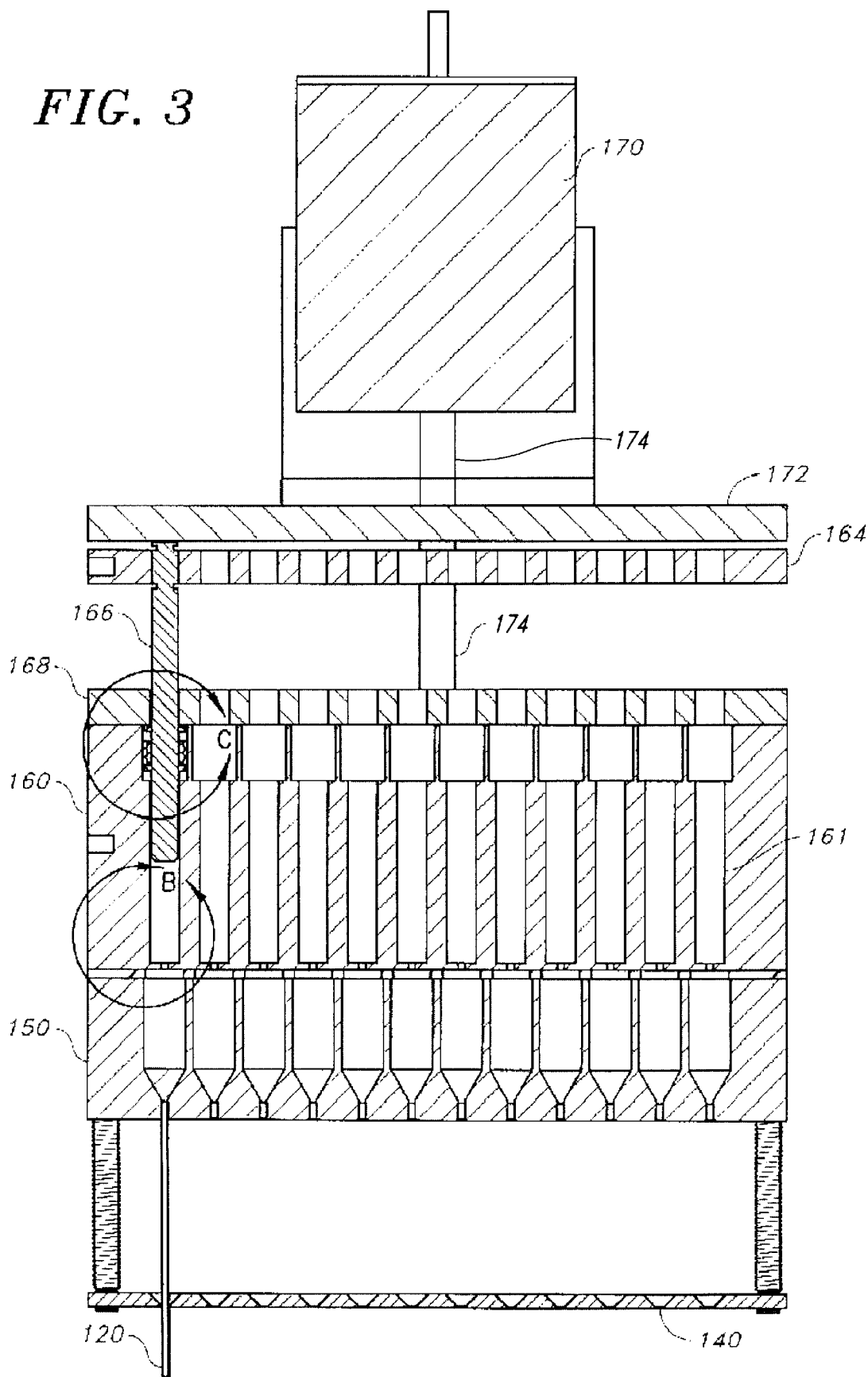
FIG. 3 shows cross section of the pipetter.

FIG. 3 shows a cross section of the pipetter and the connection of the lead screw 174 to the piston plate 164.

Figure 4:
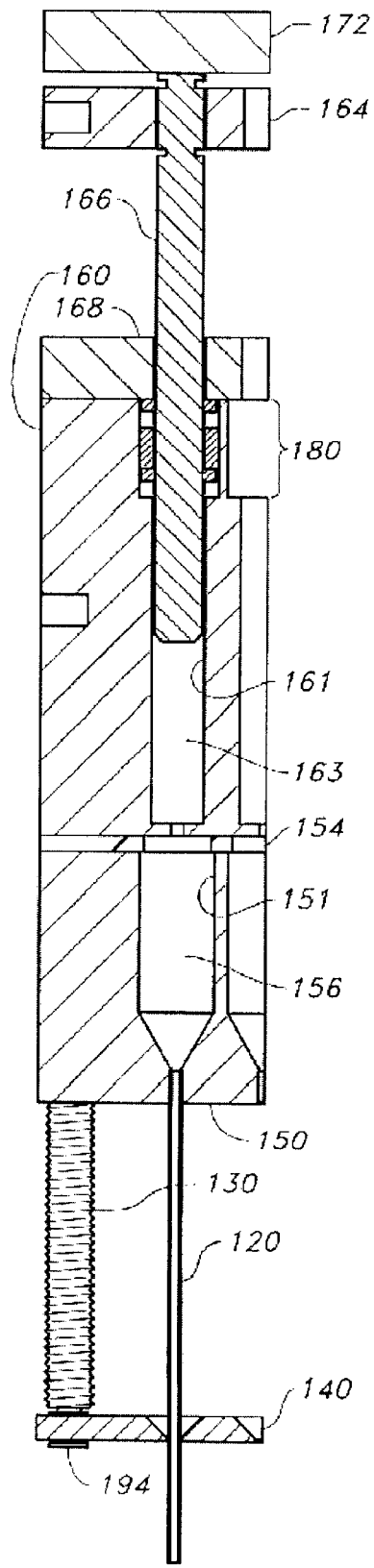
FIG. 4 is a cross section of a single pipette.

FIG. 4 is a detailed cross section of a single pipette apparatus. Starting from the bottom, there is the needle 120 positioned by needle guide plate 140. The sample volume 156 is located in the hollow cylinder 151 of sample volume block 150. Directly above the hollow cylinder 151 containing the sample volume 156 is the displacement volume 163 located in the hollow channels 161 of the displacement block 160. The vertical movement of the piston pin 166 changes the volume of air of the displacement volume 163 as the piston pin 166 moves vertically and displaces the sample volume 156 out of the needle 120. Located in between the sample displacement block 160 and the sample volume block is a sheet seal 154, preferably made of silicone. The sheet seal 154 has a plurality of holes to accommodate the plurality of the hollow channels 161 of the displacement block 160 and the hollow cylinders 151 of the sample volume block 150 in order for them to interact. The sheet seal 154 helps to avoid the cross-contamination of samples in the adjacent sample containing cylinders 151 by containing them to their respective cylinders 151. The configuration of a pipetting apparatus with a stationary seal 154 leads to extremely precise volume displacement due to the consistency of the friction on the piston 166.

Some chemical and biological samples can be quite corrosive, particularly when contacting the internal components of pipetters. Corrosion of parts in a pipetting apparatus can lead to imprecise volume and sample displacement. As a result of the density of the piston pins in the pipetting apparatus, it is very difficult to clean the pistons once samples come in contact with them. Corrosion can lead to costly repair and replacement of pipetting apparatus parts. The disclosed invention avoids the contact of samples with internal pipetting parts in a few ways. In order to avoid the piston pin 166 coming in contact with samples, the amount of potential volume of the sample chamber 156 is less than the total pin displacement of the piston pin 166. This results in the constant presence of an air cushion between the two volumes. The presence of the sheet seal 154 also avoids sample contact with the piston pin 166 and other internal parts by containing the samples in their respective cylinders 151.

Figure 5:
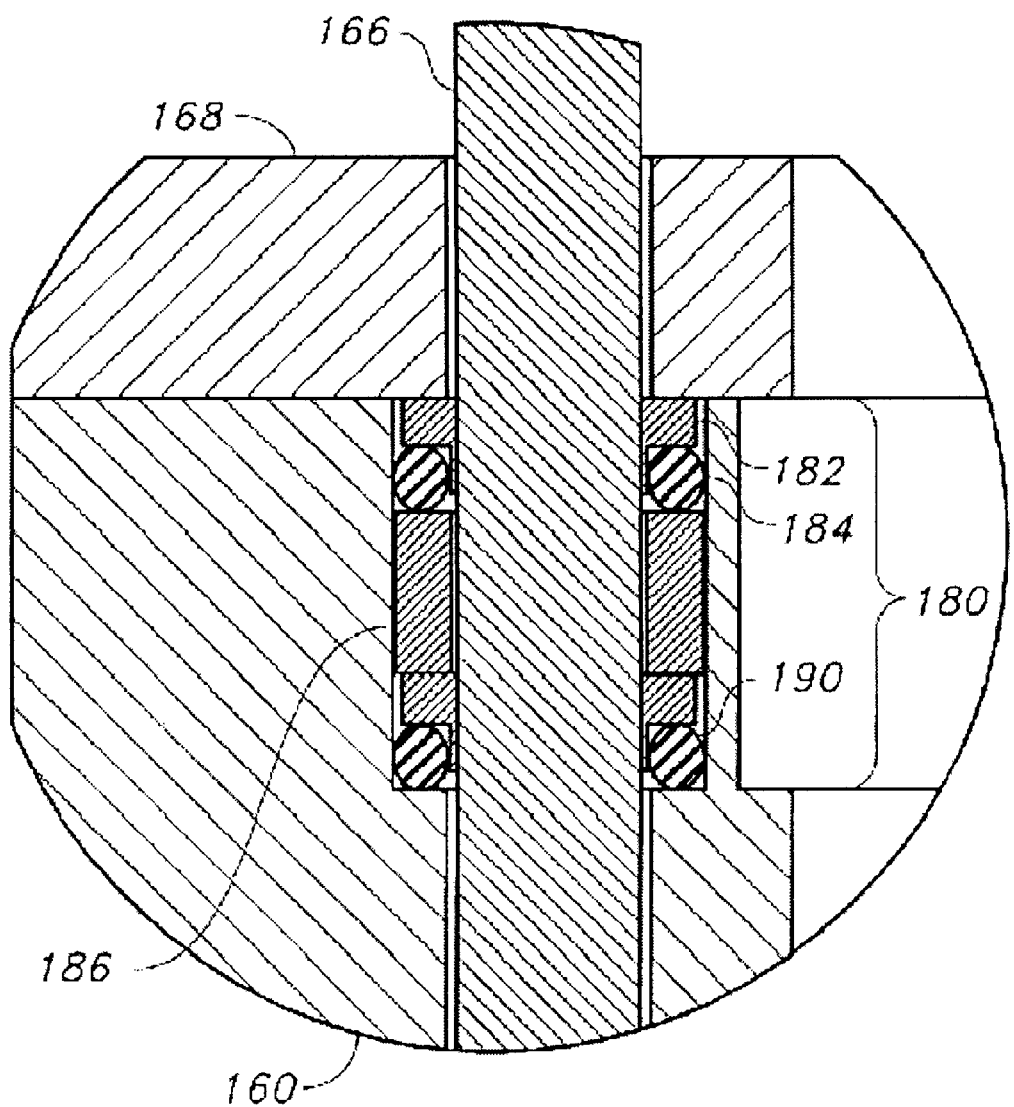
FIG. 5 is an enlargement of the seal assembly of the pipette.

In order to have precise volume dispensing and aspiration, the disclosed pipetter provides an airtight seal assembly. The seal assembly 180 is illustrated in detail in FIG. 5. In the center is piston pin 166, surrounded by seal constraint plate 168. The seal assembly 180 is located just below the seal constraint plate 168 inside a recess in displacement block 160. Each seal assembly 180 is stationary and has a hole to accommodate a piston pin 166 to slide through it. The seal assembly consists of an upper Teflon® sleeve seal 182, an upper compressed O-ring 184, a compression adjust spacer 186, a lower Teflon sleeve 188 and a lower compressed O-ring 190. The seal constraint plate 168 presses down on the upper O-rings 184, which in turn, presses on compression adjust spacers 186, which presses down on the lower O-rings 190. As a result, the O-rings are vertically compressed and expand in a horizontal direction, maintaining an airtight seal between the Teflon® sleeves, 182, 188 and the piston pin 166. The airtight seal allows for efficient sample aspiration and dispensing of precise volumes without a great amount of friction to overcome.

In addition, the seal assembly 180 avoids the cross-contamination of samples due to its precision in completely dispensing a sample from the sample volume cylinder before aspirating a new sample.

In another embodiment, the pipetting apparatus has 24 needles.

In another embodiment, the pipetting apparatus has 384 needles.

In another embodiment, the pipetting apparatus has 1536 needles.

In another embodiment, there are no crossbars.

In another embodiment, the pipetting apparatus is counter-balanced and is hand held.

In another embodiment, the pipetting apparatus is incorporated into a robotic work station for sample processing, analysis and processing.

In another embodiment, the motor is controlled by an on-board microprocessor.

EXAMPLE 1

One use for the disclosed pipetting apparatus is in conjunction with a robotic workstation (U.S. app. Ser. No. 09/494,133, filed Jan. 28, 2000, customized for the preparation of cells for cell sorting. (RevPrep™, GeneMachines, San Carlos, Calif.). Before cell sorting based on fluorescent-activated compounds, the desired cells need to be labeled with a fluorescent tag, such as a labeled antibody. The robotic configuration suitable for such cell preparation is illustrated in FIG. 6 and combines the following tools and instruments: 1) an array centrifuge, 2) a pipetter, 3) a wash station, and 4) a bulk reagent dispenser. LabVIEW™ Software (LTR Publishing, Inc., Dallas, Tex.) is programmed to run this configuration of the robotic workstation.

A pipetter is attached to the central column by a modular tool block. Microwell plates are nestled into deck locations with specially shaped holes therein. Each well of a first microwell plate contains a different cell sample or a control. A second microwell plate (not shown) contains antibodies in a plurality of its wells. The rotary deck powered by the deck motor revolves and carries the first microwell plate containing the cells, until the plate is precisely aligned underneath the pipetter. The pipetter is lowered by lead screw attached to stepper motor toward the rotary deck, and it aspirates the cells from the microwell plate. The pipetter moves vertically to its original position while the second microwell plate containing the test antibodies is then moved on the rotary deck until it is precisely aligned beneath the pipetter. The pipetter moves vertically towards the rotary deck and dispenses the cells into the plurality of wells. The combinations of cells and antibodies then incubate in the second microwell plate.

A bulk reagent dispenser is also attached to the central column via a modular tool mount block. Vertical motion of the bulk reagent dispenser is powered by a lead screw and stepper motor. The microwell plate containing the combination of antibodies and cells is moved horizontally on the rotary deck until it is precisely aligned with the bulk reagent dispenser. The bulk reagent dispenser moves vertically towards the rotary deck and deposits wash solution into the plurality of wells of the microwell plate. Then the bulk reagent dispenser moves back up to its original position, as the second microwell plate containing the combination of solutions is horizontally moved until it precisely aligns with the pipetter. The pipetter moves vertically and aspirates the combined solutions.

An array centrifuge with a plurality of wells is located on the rotary deck. The rotary deck, powered by the deck motor, revolves and places the array centrifuge in a position precisely below the pipetter. The pipetter moves down and dispenses the diluted, incubated combinations into a plurality of wells in the microarray centrifuge. While the pipetter moves up, the array centrifuge is actuated, and the centrifugal force forms a supernatant and a cell pellet in each well. As the array centrifuge comes to a complete stop, the pipetter is then vertically moved to aspirate the supernatant from the plurality of wells of the microarray centrifuge. The pipetter moves vertically back to its original position.

A wash station occupies position on the rotary deck. The rotary deck is then moved in a horizontal direction until the wash station is precisely positioned below the pipetter. The pipetter is then vertically moved towards the wash station and dispenses the supernatant into it and washes the pipettes as well, by aspirating and dispensing repeatedly. The pipetter is then vertically moved back to its original position.

The array centrifuge is vertically moved until it is precisely aligned with the bulk reagent dispenser. The bulk reagent dispenser moves vertically and deposits wash reagent into the plurality of wells of the array centrifuge. As the bulk reagent dispenser moves vertically to its original position, the array centrifuge resuspends the cell pellet by rapid changes in its rotational velocity. The array centrifuge then centrifuges the mixture once again to separate a supernatant and a cell pellet. As the array centrifuge slows down, the deck moves to align the array centrifuge with the pipetter. The supernatant is removed by the pipetter and dispensed into the wash station, and then the bulk reagent dispenser adds more wash reagent into the array centrifuge. The addition of a wash, resuspension of the cell pellet, centrifugation, and removal of a supernatant is repeated three times. After the completion of these steps, a clean cell pellet remains in the array centrifuge.

The array centrifuge is horizontally moved and precisely aligned with the bulk reagent dispenser, and a labeling buffer is deposited into a plurality of wells of the array centrifuge. The array centrifuge then resuspends the cell pellet into the labeling buffer by rapid changes in its rotational velocity. This combination of substances is incubated for one hour in the array centrifuge, or it can be removed and placed in a microwell plate for the incubation period.

Once again, the bulk reagent dispenser adds wash reagent to the incubated substance. This incubated substance is then centrifuged. The supernatant is removed by the pipetter and disposed of in the wash station 204. More wash reagent is added to a plurality of the array centrifuge wells; then there is resuspension and then centrifugation. The cycle of adding a wash reagent, resuspending, centrifuging and removing a supernatant is repeated twice.

The array centrifuge is then realigned with the bulk reagent dispenser and a re-suspension and fixing solution is added to the wells. This mixture is resuspended. This solution is then removed by the pipetter and placed into an appropriate container for cell sorting.

It is to be understood that the above description is intended to be illustrative and not restrictive. Many embodiments will be apparent to those of skill in the art upon reviewing the above description. The scope of the invention should be determined not with reference to the above description but should instead be determined with reference to the appended claims, along with the full scope of equivalents to which such claims are entitled.

We claim:

1. A micropipetter comprising
   a. a plurality of hollow needles to deliver fluid, said needles being anchored in a sample block;
   b. a needle guide assembly comprising a plurality of needle guide shafts and compression springs, each attached at one end to the sample block and at the other end to a needle guide plate, each spring surrounding a needle guide shaft, and the needle guide plate guiding the spacing of the needles;
   c. a sample block having a plurality of hollow spaces, each of which connect with the hollow needle;
   d. a displacement volume block having a plurality of hollow spaces, each being occupied by a piston pin, each piston pin being sealed with a stationary seal assembly;
   e. a stationary sheet seal located between the sample block and the displacement volume block, the sheet seal having a plurality of holes corresponding to and separating the spaces in the sample block and the displacement volume block, such that precise volume displacement is provided;
   f. a seal constraint plate located above the displacement volume block, the seal constraint plate being positioned to hold in place an airtight, low-friction seal assembly around each of the piston pins;
   g. the piston pins being attached to a piston pin plate; and
   h. motive means for moving the pistons vertically and thereby alternately aspirating fluid into the needles and dispensing fluid from the needles.

2. The micropipetter of claim 1, wherein the seal assembly comprises an upper sleeve which is in contact with the piston pin, an upper O-ring which is positioned between the upper sleeve and a compression-adjust spacer, a lower sleeve and a lower O-ring which is positioned between the lower sleeve and the compression-adjust spacer.

3. The micropipetter of claim 2, wherein the upper and lower sleeves are Teflon.

4. The micropipetter of claim 1, wherein the seal assembly comprises upper and lower sleeves and two intervening O-rings.

5. The micropipetter of claim 1, wherein the seal assembly comprises one sleeve and one O-ring.

6. The micropipetter of claim 1, wherein the motive means comprises at least one motor having at least one lead-screw drive which goes through the core of the motor, the lead-screw drive being attached to an armature, such that actuating the motor causes the lead-screw drive to pull up or lower the rest of the micropipetter.

7. The micropipetter of claim 1, further comprising at least one set of crossbars, each crossbar being attached to the constraint plate and the piston pin plate, thereby increasing stability of the micropipetter and aiding in precise movement.

8. The micropipetter of claim 1, wherein the plurality of hollow needles numbers 1, 8, 16, 24, 96, 384, or 1536.

9. The micropipetter of claim 1, further comprising a counter-balance to aid in hand-held use.

10. The micropipetter of claim 1, incorporated into a robotic workstation.

11. The micropipetter of claim 1, wherein the motive means is controlled by an on-board microprocessor.

* * * * *